United States Patent
Barness et al.

(10) Patent No.: US 7,618,616 B2
(45) Date of Patent: Nov. 17, 2009

(54) SKIN-PROTECTIVE COMPOSITIONS EFFECTIVE AGAINST VESICANTS AND PERCUTANEOUS CHEMICAL AGENTS

(75) Inventors: Itzhak Barness, Kiron (IL); Tamar Kadar, Rishon Lezion (IL); Eliezer Fishbine, Ness-Ziona (IL)

(73) Assignee: State of Israel Prime Minister's Office-Israel Institute of Biological Research, Ness Ziona (IL)

( * ) Notice: Subject to any disclaimer, the term of this patent is extended or adjusted under 35 U.S.C. 154(b) by 778 days.

(21) Appl. No.: 10/475,878

(22) PCT Filed: Dec. 31, 2001

(86) PCT No.: PCT/IL01/01222

§ 371 (c)(1),
(2), (4) Date: Apr. 5, 2004

(87) PCT Pub. No.: WO02/085322

PCT Pub. Date: Oct. 31, 2002

(65) Prior Publication Data

US 2004/0235756 A1 Nov. 25, 2004

(30) Foreign Application Priority Data

Apr. 25, 2001 (IL) .................................. 142812

(51) Int. Cl.
*A61K 8/73* (2006.01)
(52) U.S. Cl. ............... 424/70.13; 442/122; 510/110
(58) Field of Classification Search ........... 424/70.13, 424/400, 401; 422/28, 1
See application file for complete search history.

(56) References Cited

U.S. PATENT DOCUMENTS

| | | | |
|---|---|---|---|
| 4,107,330 A | 8/1978 | Sheffner | |
| 4,259,318 A | 3/1981 | Duhe | |
| 4,465,663 A | 8/1984 | Schmolka | |
| 4,683,244 A * | 7/1987 | Moeller et al. | 514/568 |
| 4,850,729 A * | 7/1989 | Kramer et al. | 401/183 |
| 5,034,226 A * | 7/1991 | Beck | 424/401 |
| 5,162,378 A | 11/1992 | Guthauser | |
| 5,221,533 A | 6/1993 | Perlman | |
| 5,512,278 A | 4/1996 | Mundschenk | |
| 5,607,979 A | 3/1997 | McCreery | |
| 5,695,775 A * | 12/1997 | von Blucher et al. | 424/405 |
| 5,702,709 A | 12/1997 | Schulz | |
| 5,703,104 A | 12/1997 | Peck | |
| 5,753,270 A * | 5/1998 | Beauchamp et al. | 424/667 |
| 5,780,618 A | 7/1998 | Banker et al. | |
| 5,837,266 A | 11/1998 | Toma | |
| 5,851,540 A | 12/1998 | Toma | |
| 5,888,520 A | 3/1999 | Toma | |
| 6,110,475 A | 8/2000 | Toma | |
| 6,224,885 B1 | 5/2001 | Jenner et al. | |

FOREIGN PATENT DOCUMENTS

| | | |
|---|---|---|
| DE | 470954 | 10/1924 |
| EP | 545002 | 6/1993 |
| EP | 1064908 | 1/2001 |
| EP | 1214932 | 6/2002 |
| FR | 2689021 | 10/1993 |
| GB | 2237739 | 5/1991 |
| JP | 6-279265 | 10/1994 |
| WO | WO 97/03057 | 1/1997 |
| WO | WO 97/40813 | 11/1997 |
| WO | WO 97/42934 | 11/1997 |
| WO | WO 97/44007 | 11/1997 |
| WO | WO 99/49841 | 10/1999 |
| WO | WO 01/05226 | 1/2001 |

OTHER PUBLICATIONS

Europaisches Arzneibuch 1997 Deutscher Apotheker Verlag, Stuttgart, XP002207570, p. 998.
Written Opinion for PCT/IL01/012222, mailed Jan. 15, 2003, eight pages.
International Search Report for PCT/IL01/01222 (4 pages) mailed Sep. 8, 2002.
International Preliminary Examination Report for PCT/IL01/012222 (12 pages—report and amended claims) mailed Mar. 9, 2003.
Principles and practice of modern cosmetics, Modern Cosmeticology, vol. 1, 1962, p. 663.
Principles and practice of modern cosmetics, Cosmetic Materials, vol. 2, 1963, pp. 202-205.

* cited by examiner

*Primary Examiner*—Michael G. Hartley
*Assistant Examiner*—James W. Rogers
(74) *Attorney, Agent, or Firm*—Roach Brown McCarthy & Gruber, P.C.; Kevin D. McCarthy

(57) ABSTRACT

A protective agent suitable to protect the human skin against lesions caused by vesicants or other percutaneous chemical agents, particularly against sulfur mustard gas injury and VX intoxication, which comprises a protective-effective amount of a hydrophilic water-based cream, alone or together with one or more additives selected from among the group consisting essentially of polyols, mono-, oligo- or polysaccharides, and salts of organic or inorganic acids. The additive polyol may be glycol, propylene glycol, polyglycerol, glycerin, sorbitol, dulcitol, tritol, sorbitol or mannitol. The additive monosaccharide may be ribose, xylose, glucose, fructose, galactose or mannose. The additive oligosaccharide may be sucrose, maltose, lactose, raffinose or cellobiose.

3 Claims, 1 Drawing Sheet

SKIN-PROTECTIVE COMPOSITIONS EFFECTIVE AGAINST VESICANTS AND PERCUTANEOUS CHEMICAL AGENTS

FIELD OF THE INVENTION

The invention relates to protective compositions for protecting the skin against damages caused by sulfur mustard gas and other chemical agents, such as VX, pesticides, nitrogen mustard and poison ivy.

BACKGROUND OF THE INVENTION

Sulfur mustard (both in gaseous and liquid form) is a potent cutaneous vesicant which rapidly penetrates the skin and causes prolonged injuries, and is therefore representative of the percutaneous agents to the protection against which the present invention is directed. Sulfur

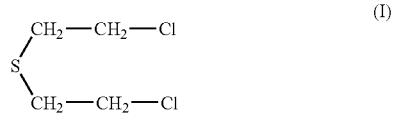

mustard, as an example of major hazards consists of β-chlorodiethylsulfide of the formula:

which may further contain other components, such as other active compounds.

VX as an example for nerve agent: O-ethyl-S-(2-diisopropylaminoethyl-methylphosphothiolate), of the formula:

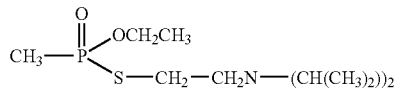

There are two main ways known in the art of protecting a person's skin against chemical warfare agents such as mustard: The first method is a passive protection which involves covering the skin with a protective cover, such as a protective cloth. This method has several drawbacks: firstly, the protective clothings are heavy and uncomfortable to wear for a long period of time, and therefore they cannot be continuously worn as a preventive measure. Secondly, the protective covers leave areas unprotected, such as the hands and neck, and therefore do not offer complete protection. Furthermore, such protective measures are quite expensive, which of course limits their usefulness.

The second method involves applying reactive materials to the skin, which react with the sulfur mustard gas and neutralize it. The drawback associated with this method is that it requires to apply to the skin active materials which generally are in themselves harmful, typically require the application of oily and uncomfortable materials to the skin, and furthermore are as yet only limited in efficacy. Additionally, such reactive materials are also generally required in large amounts, which are difficult to apply to the skin.

Other protections, which involve the use of creams which promote the creation of a polymeric film on the skin are also not very effective, since the film cracks and leaves areas below the cracks exposed. Furthermore, such films are thick and uncomfortable to the user. Another cream exists, which penetrates the skin, leaving an outer layer that can act as a matrix for active protecting agents. This cream also exhibits the drawbacks described above. In addition, this protective cream requires a thick layer to be applied. The above composition may be toxic to the respiratory system due to fumes emerging from smoking products, such as cigarettes, and thus it is not effective in hot environments or where fire is present.

The art, notwithstanding the many efforts devoted to the solution of this problem, has failed so far to provide a solution to the above problem, viz., a protection for the skin which overcomes the above drawbacks.

It is therefore an object of this invention to provide a protective agent which is effective against sulfur mustard and other chemical agents, such as VX, and which overcomes the drawbacks of prior art protections.

It is another purpose of this invention to provide a protective agent which can be applied to the skin often, which does not lead to discomfort, and which is not harmful to the skin.

It is yet another purpose of the invention to provide a protective agent which remains effective for a long period of time after application, in the order of 6-12 hours before exposure to the harmful chemical agent.

Other purposes and advantages of this invention will appear as the description proceeds.

SUMMARY OF THE INVENTION

The invention is directed to a protective agent suitable to protect the human skin against sulfur mustard gas injury, nerve agents such as VX and injury from other harmful chemical agents, comprising a protective-effective amount of a hydrophilic water-based cream, alone or together with one or more additives selected from among the group consisting essentially of polyols, mono-, oligo- or polysaccharides, salts of organic or inorganic acids, and absorbant compounds.

The term "cream", as used herein, is intended to indicate any preparation of sufficient viscosity to remain on the skin for a sufficient period of time so as to be absorbed into its surface, and should be understood to include also preparations of appearance other than creamy, such as lotions or ointments.

According to a preferred embodiment of the invention the additive polyol is selected from among polyethylene glycol, propylene glycol, polyglycerol, glycerin, sorbitol, dulcitol, tritol, sorbitol or mannitol.

According to another preferred embodiment of the invention the additive monosaccharide is selected from among arabinose, ribose, xylose, glucose, fructose, galactose and mannose.

According to still another preferred embodiment of the invention the synergistic additive oligosaccharide is selected from among sucrose, maltose, lactose, raffinose or cellobiose.

According to yet another preferred embodiment of the invention the additive polysaccharide is selected from among starch or gum arabicum.

The protective agent may contain, according to another preferred embodiment of the invention, an additive salt selected from among salts of citric acid, glycolic acid, gluconic acid, tartaric acid, glucaric acid, glyceric acid, lactic acid, ascorbic acid, thioglycolic acid, benzoic acid, acetic acid, glycine, alanine, serine, lysine, aspartic acid, cysteine, proline, glutamic acid, δ-hydroxylysine, glutamine or urea.

The hydrophilic water-based cream of the invention may be of different types, the important requirements from such base cream being its hydrophilic nature, and its ability to be spread on the skin and accepted thereby. For this purpose, glycerin is particularly suitable, since it is absorbed into the skin and interacts with the epidermis, to provide a homogeneous and long-lasting protective layer which effectively protects the skin against sulfur mustard, VX and other chemical insults, even in the absence of additives.

Without wishing to be bound by any particular theory, it is the inventor's belief that the action of the cream of the invention is due to its hydrophilic behavior, which repels sulfur mustard from the skin surface. The addition of hydrophilic additives of the kind employed in this invention, further enhance this phenomenon and creates a "salting-out-like" effect toward the sulfur mustard and other chemical agents. Thus, for instance, the addition of salts to the cream displaces water molecules and caused a repulsion of the sulfur mustard or other toxic organic agents away from the skin.

While, as stated, glycerin is the preferred base for the protective agent cream, other bases can be used. Cream is defined for the present invention as a composition having viscosity significantly higher than water. For example, the viscosity of glycerin is 1490-629 centipoise between 20-30° C., respectively, sorbitol viscosity 110 centipoise at 25° C., while water viscosity is 1.8 centipoise at 25° C. According to a preferred embodiment of the invention the hydrophilic water-based cream contains one or more additives, and the water-based cream consists essentially of a material selected from among monosaccharides such as sorbitol, potassium gluconate, potassium tartarate, potassium citrate, calcium chloride or potassium carbonate. As stated, and as will be further detailed hereinafter, the cream may contain additional salts, such as $MgSO_4$ or other organic salts, or inorganic salts such as aluminum salts, $MgCl_2$ or $CaCl_2$, provided that no reaction or precipitation takes place between them, or surface active agents such as Triton X100, esters of sugars and lecithin.

While the presence of active materials is not a necessity in the protective agents of the invention, any suitable active agent can be added. For instance, the protective agent of the invention may further comprise antiseptic materials. Furthermore, the protective agent may further comprise reactive materials, such as nucleophilic materials, e.g., thiosulphate, or adsorbent compounds such as bentonite, silica gel, zeolites. Illustrative and non-limitative examples of reactive materials include, e.g., dithiophosphate ion, ethanedithiophosphate ion, hexanedithiophosphate ion, butyldithiophosphate ion, ethyldithiophosphate ion, pentaethylenedithiocarbamate, thiosulphate ion and dialkylthiophosphate.

Additional reactive agents that may be added to the protective cream are oxidizing materials. Unstable materials, such as $H_2O_2$, may be added on the spot and may be provided separately from the protective cream. Other oxidizing agents may be included in the protective cream. Illustrative and non-limitative examples of oxidizing agents are: perchlorides, peroxides, sodium percarbonate, $H_2O_2$: urea complex, $H_2O_2$: PVP (polyvinylpyrrolidone) complex and magnesium monoperoxy phthalate.

Non-reactive agents may include, for instance, thickening agents such as methylcellulose, xanthan, carboxy methyl cellulose (CMC), etc.

In another aspect, therefore, the invention is directed to a method for protecting the human skin against percutaneous chemical agents such as sulfur mustard, comprising applying to the skin a protective-effective amount of a hydrophilic water-based cream, alone or together with one or more additives selected from among the group consisting essentially of polyols, mono-, oligo- or polysaccharides, and salts of organic or inorganic acids.

DETAILED DESCRIPTION OF PREFERRED EMBODIMENTS

Figure 1:
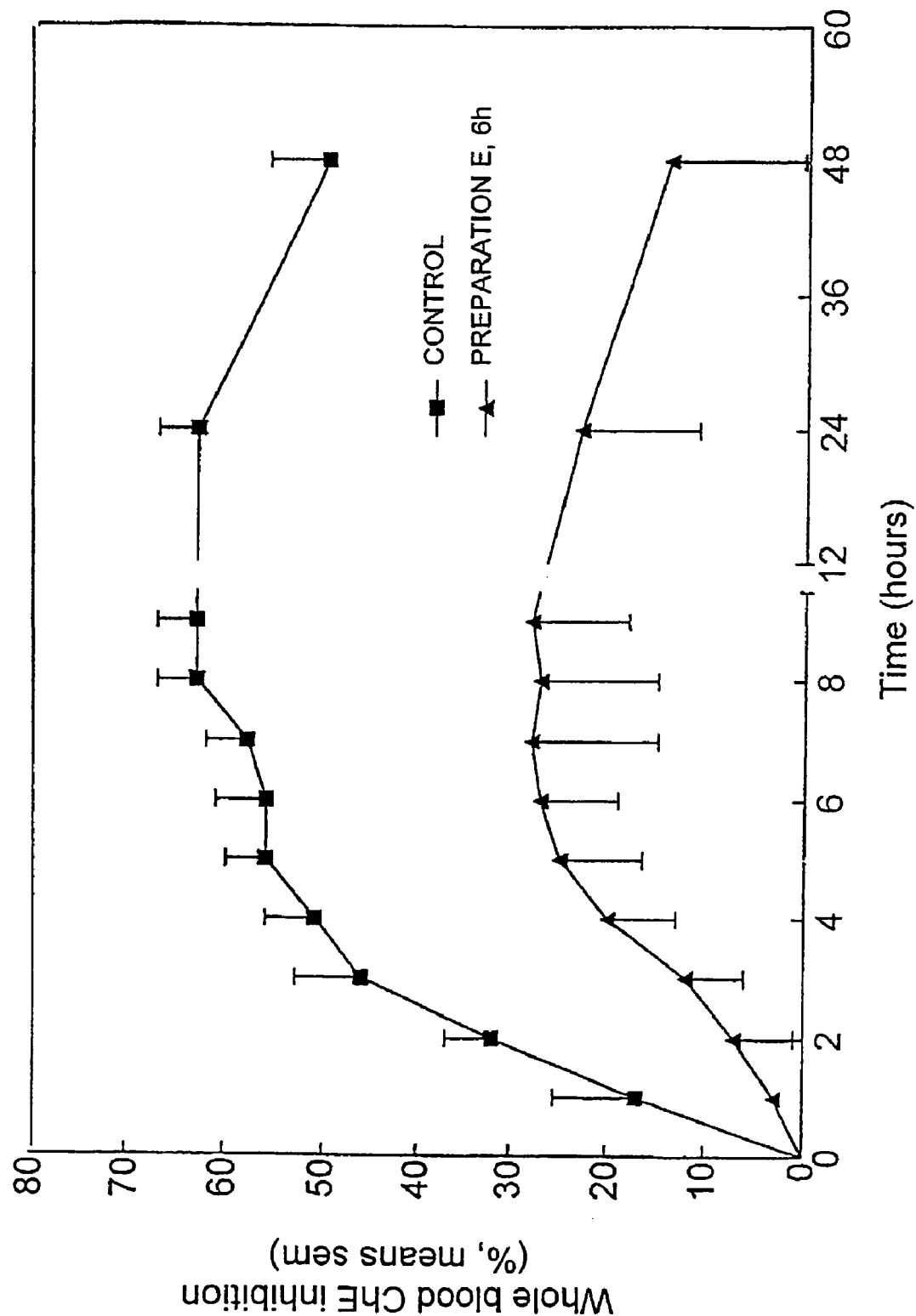
FIG. 1 is a graphical description of the results obtained in Example 2.

The above and other characteristics and advantages of the invention will be better understood through the following illustrative and non-limitative examples of preferred embodiments thereof.

General Procedures

Protective creams were tested for efficacy against sulfur mustard lesions and VX poisoning. The protective potential was tested either against 0.2 and 1 microliter droplets of sulfur mustard applied topically on the back of pigs' skin, or sulfur mustard vapor or VX (0.2 and 1 microliters). The extent of cutaneous lesion following liquid sulfur mustard was evaluated quantitatively using a morphometric and densitometric method with the aid of an image analyzer.

The area of the damaged skin was measured at 24 hours post exposure and the protective value of each cream was calculated as a percent of control of sulfur mustard lesion (0% protection representing identity to the sulfur mustard lesion). The same test was carried out under sweating conditions in pigs, and gave almost identical results. When tested against VX poisoning in pigs, the leathality and clinical signs were monitored and the percent inhibition of acetylcholinesterase (AChE) activity was measured in blood samples. All the pigs pretreated with the protective creams survived a 1-5 hours challenge with lethal concentrations (twice the $LD_{50}$) of VX and did not exhibit any clinical signs, up to three hours exposure challenges. In comparison, in the absence of the protective cream, all animals had severe clinical symptoms and the majority died within 24-48 hours after exposure to VX. AChE activity was significantly higher in all animals pretreated with the cream, compared to unprotected animals. However, some decline in blood AChE activity, induced by dermal application of VX (1.3 mg/Kg, 1 µl) in pigs was measured in the treated animals (see Example 2 and FIG. 1). The protective creams provided a significant protection, even when applied 12 hours (single application) prior to a one hour challenge with 1 µl droplets of VX (2 $LD_{50}$), or sulfur mustard, when $LD_{50}$=0.65 mg/Kg in pigs, for VX.

Five formulations were tested for irritation in controlled laboratory studies, and were found to be non-irritating by the Draize procedure in guinea pigs and rabbits. Three preparations were tested also in Phase I clinical study, with young male healthy volunteers. The creams were applied on about 20% of the skin surface. The preparations were found to be non-irritating and safe for human use.

Preparation A

A cream composition containing potassium citrate was prepared using the following components:

| | |
|---|---|
| Citric acid monohydrate, 99% (ex Aldrich) | 10.5 gr |
| KOH, 86% (ex Fluka) | 8.4 gr |
| Distilled water | 5.0 gr |
| Glycerin 87% (ex Merck) | 20.0 gr |

Comparable results were obtained when Glycerin 100% was used.

Preparation B

A cream composition containing potassium acetate was prepared using the following components:

| | |
|---|---|
| Potassium acetate (ex Hopkin & Williams) | 30.0 gr |
| Glycerin 87% (ex Merck) | 20.0 gr |

Preparation C

A cream composition containing sorbitol was prepared using the following components:

| | |
|---|---|
| Sorbitol (ex BDH) | 30.0 gr |
| Distilled water | 9.0 gr |
| Glycerin 87% (ex Merck) | 15.0 gr |

Preparation D

A cream composition containing potassium β-alanine was prepared using the following components:

| | |
|---|---|
| β-alanine, 98% (ex Aldrich) | 8.9 gr |
| KOH, 86% (ex Fluka) | 5.6 gr |
| Distilled water | 5.0 gr |
| Glycerin 87% (ex Merck) | 10.0 gr |

Preparation E

A cream composition containing magnesium sulfate was prepared using the following components:

| | |
|---|---|
| Magnesium sulfate | 10.0 gr |
| Glycerin 87% (ex Merck) | 30.0 gr |

Preparation F

A cream composition containing potassium borate was prepared using the following components:

| | |
|---|---|
| Sodium borate ($Na_2B_4O_7 \cdot 10H_2O$) | 20.0 gr |
| Glycerin 87% (ex Merck) | 30.0 gr |

Preparation G

A cream composition containing glycerin was prepared containing only glycerin 87%.

Preparation H

| | |
|---|---|
| Magnesium sulfate·$7H_2O$ | 1.5 gr |
| Glycerin 87% | 4.5 gr |
| Silica gel | 2 gr |
| Manoxol OT (dioctyl ester of sodium sulfusuccinic acid) | 30 mg |

Alternative Surface Active Agents
Manoxol OT
Triton x 100
Lecithine
Sodium Lauryl Sulfate Alternative Adsorbants
Bentonite
Fumed silica gel
Silica gel
Nanosize- MgO, ZnO, $Al_2O_3$, $TiO_2$
Zeolites
Activated charcoal

EXAMPLE 1

The efficacy of various protective compositions of the invention were tested according to the general procedure described above. The results are summarized in Table I below:

TABLE I

| | | Exposure and Protection | | | | | |
|---|---|---|---|---|---|---|---|
| | | 0.2 μl | | 1 μl | | | |
| Protective Compositions In Glycerin 87% | Ratio C:w:g[1] | 10 mins* 3 hrs** | 30 mins 3 hrs** | 10 mins 3 hrs** | 30 mins 3 hrs** | 60 mins 3 hrs** | 60 mins* 6 hrs** |
| | | | | Protection (%) | | | |
| Potassium Lactate | 40:0:60 | 94 | | | | | |
| Potassium Gluconate | | 85 | | | | | |
| Potassium Tartarate | 15:7.5:7.5 | 100 | 94 | | 97 | 92 | 90 |
| Potassium Citrate | | 100 | 100 | 100 | 97 | 88 | 88 |
| Potassium Acetate | | 100 | 90 | | | | |
| Sodium-OTC[b] | 5:40:1.5[a] | 85 | | | | | |
| Potassium Carbonate | | 100 | | | | | |
| Sodium Borate | | 100 | | | | | |
| Sodium Silicate | 1:0:1 | 100 | 100 | | 94 | | |
| Magnesium Sulfate | 15:7.5:7.5 | 100 | 90 | | 91 | 85 | 89 |
| Calcium Chloride | 10:5:5 | 91 | | | 99 | | |
| Sodium Thiosulfate/Water | | 69 | | | | | |
| Sodium Chloride | 20:0:80 | 70 | | | | | |
| Sodium Chloride/Water | | 48 | | | | | |
| Potassium β-alanine | | 100 | 93 | | 97 | 90 | 90 |

TABLE I-continued

| | | Exposure and Protection | | | | | |
| | | 0.2 μl | | 1 μl | | | |
| Protective Compositions In Glycerin 87% | Ratio C:w:g[1] | 10 mins* 3 hrs** | 30 mins 3 hrs** | 10 mins 3 hrs** | 30 mins 3 hrs** | 60 mins 3 hrs** | 60 mins* 6 hrs** |
| --- | --- | --- | --- | --- | --- | --- | --- |
| | | | | Protection (%) | | | |
| Sorbitol | | | | | 99 | 90 | 90 |
| Glycerin 87% | | | 84 | | 91 | 85 | 85 |
| Glycerin 15% | | | | | | 80 | |
| Glycerin 5% | | | | | | 80 | |

*Time of exposure to liquid sulfur mustard
**Time of application of protective agent prior to exposure
[1]Ratio cream component:water:glycerin
[a]NaOH
[b]R-oxothiazolidine-4-carboxylate

EXAMPLE 2

The efficacy of preparation E against VX challenge (twice the $LD_{50}$, $LD_{50}$=0.65 mg/Kg in pigs) was tested in pigs according to the procedure described above. The results of one of the experiments, where the cream of preparation E was dermally applied once, 6 hours before a one hour challenge with 1.3 mg/Kg VX (1 μl) are shown in FIG. 1.

While embodiments of the invention have been described by way of illustration, it will be understood that the invention can be carried out by persons skilled in the art with many modifications, variations and adaptations, without departing from its spirit or exceeding the scope of the claims.

The invention claimed is:

1. A method for protecting the human skin against injury caused by vesicants or nerve agents, comprising applying onto the skin, before its exposure to said vesicants or nerve agents, a protective-effective amount of a hydrophilic glycerin-based lipid-free cream, consisting of glycerin and water.

2. A method according to claim 1, wherein said vesicant is sulfur mustard gas.

3. A method according to claim 1, wherein said nerve agent is VX.

* * * * *